United States Patent [19]

Kelly et al.

[11] 4,245,652

[45] Jan. 20, 1981

[54] DEVICE AND METHOD FOR PREVENTING FOREIGN SUBSTANCE MIGRATION THROUGH AN OPENING IN LIVING ANIMAL TISSUE

[75] Inventors: Leonard T. Kelly, Carson, Calif.; Esther V. M. Hamel, St. Ignatius, Mont.

[73] Assignee: Hamelly International, Inc., St. Ignatius, Mont.

[21] Appl. No.: 949,910

[22] Filed: Oct. 10, 1978

[51] Int. Cl.³ .............................................. A61B 19/00

[52] U.S. Cl. .................................... 128/736; 128/283; 128/348; 116/DIG. 34

[58] Field of Search ............... 128/1 R, 283, 348-351, 128/246, 736; 116/DIG. 34; 85/62

[56] References Cited

U.S. PATENT DOCUMENTS

| | | | |
|---|---|---|---|
| 1,188,180 | 6/1916 | Kells | 128/350 R |
| 2,457,244 | 12/1948 | Lamson | 128/1 R |
| 2,874,697 | 2/1959 | Johnson | 128/283 |
| 3,021,747 | 2/1962 | Garrett | 116/DIG. 34 |
| 3,077,192 | 2/1963 | Berger | 128/283 |
| 3,153,974 | 10/1964 | Canning | 85/62 |
| 3,707,146 | 12/1972 | Cook et al. | 128/246 X |
| 3,712,304 | 1/1973 | Marsan | 128/283 |
| 3,713,445 | 1/1973 | Marsan | 128/283 |
| 4,069,826 | 1/1978 | Sessions et al. | 128/348 |
| 4,083,364 | 4/1978 | Kelly et al. | 128/736 |
| 4,094,303 | 6/1978 | Johnson | 128/1 R |

FOREIGN PATENT DOCUMENTS

| | | | |
|---|---|---|---|
| 1274374 | 5/1972 | United Kingdom | 128/283 |
| 141591 | 1/1961 | U.S.S.R. | 128/350 R |

*Primary Examiner*—Dalton L. Truluck

*Attorney, Agent, or Firm*—Robert J. Schaap

[57] ABSTRACT

A relatively permanent barrier device which serves as a barrier to migration of foreign substances, as for example, bacteria or other disease promoting agents, through an opening in living animal tissue. The barrier device also aids in promoting healing of the animal tissue around the opening. In a preferred embodiment, the opening is designed to receive a percutaneous member or similar member for relatively permanent implant in the animal. Generally, the percutaneous member includes a stem which is insertable through the opening and into the subcutaneous facia of the animal with an enlarged head capable of overlying and engaging a portion of the barrier element. This member includes a fastening element shiftable into engagement with a portion of the animal tissue to retentively hold the member in the animal. The barrier device comprises a flexible and relatively compressible element capable of being sufficiently deformable to fully conform to the surface of the animal with which it is in contact and to fully cover the opening in the animal tissue. Thus, the barrier device is sufficiently resilient so as to always engage the surface of the animal tissue surrounding the opening even during any shifting movement or displacement of the animal tissue. The element will also partially conform to a portion of the percutaneous member which is in contact with the barrier element. The barrier device is generally permanently retained about the opening in said animal tissue by the percutaneous member or other retaining member. The compressible nature of the barrier element also allows it to effectively serve as an indication of tightness with which the percutaneous member is held within the animal and to aid in obviating any problem of necrosis.

7 Claims, 7 Drawing Figures

FIG. 1
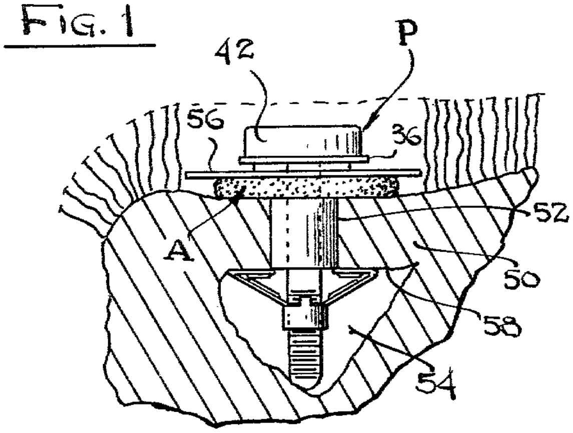
FIG. 7
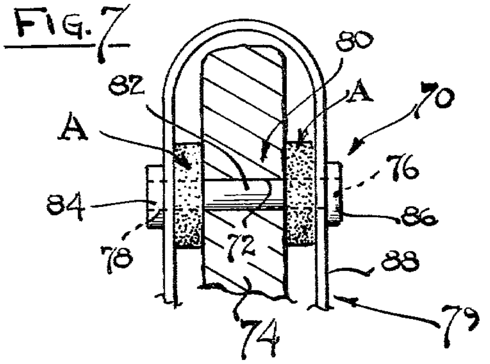
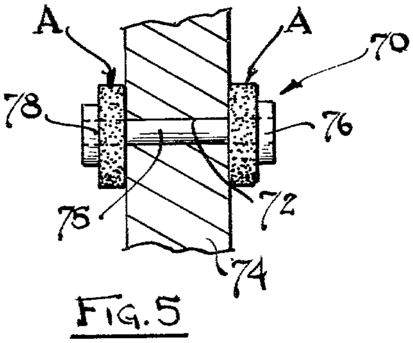
FIG. 5
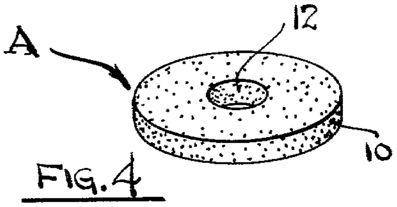
FIG. 4
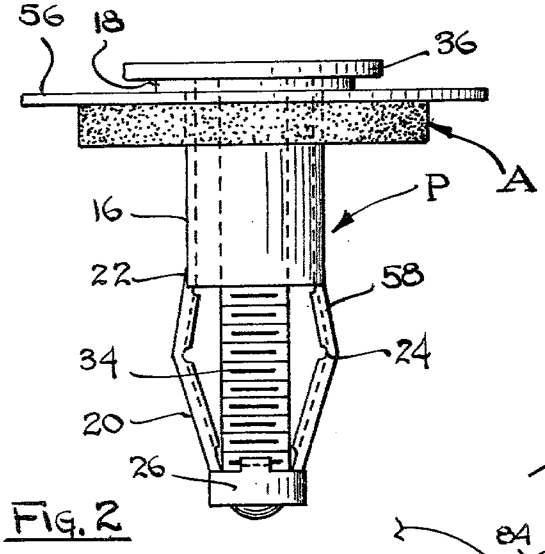
FIG. 2
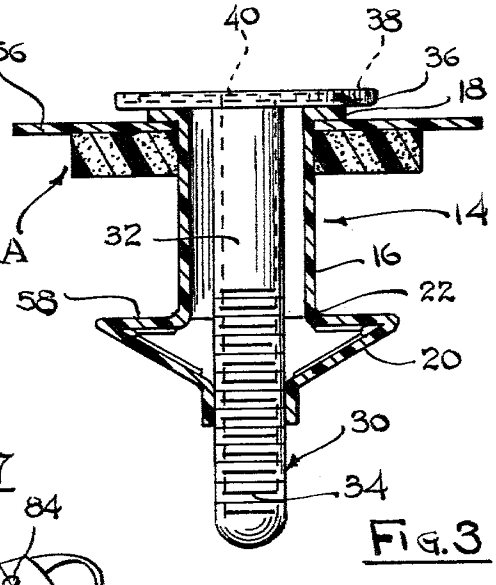
FIG. 3
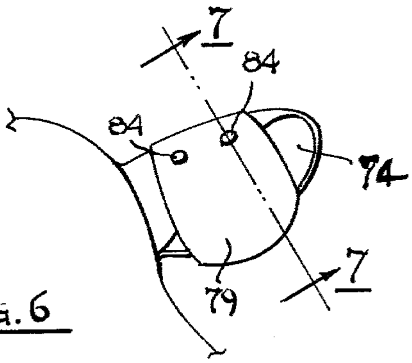
FIG. 6

DEVICE AND METHOD FOR PREVENTING FOREIGN SUBSTANCE MIGRATION THROUGH AN OPENING IN LIVING ANIMAL TISSUE

BACKGROUND OF THE INVENTION

1. Field of the Invention

This invention relates in general to certain new and useful improvements in barrier devices which serve as a barrier to foreign substance migration throughout an opening in living animal tissue, and, more particularly, to barrier devices of the type stated which are formed of a flexible, resilient element capable of being deformable to conform to the surface of an animal and fully cover an opening in animal tissue and to also provide visual indication of the amount of tightness with which a rigid, or somewhat rigid, member is held in animal tissue.

2. Brief Description of the Prior Art

There have been several in-vivo temperature indicating devices which provide visual indication of temperature changes in generally domestic and semi-domestic animals, as for example, cattle. This information is valuable since the temperature changes may be indicative of a disease producing pathogen present in the animal. One such device, for example, is described in U.S. Pat. No. 3,889,658 to Newhall. Another device providing indication of temperature change is described in U.S. Pat. No. 4,083,364 to Kelly et al.

It is, of course, highly desirable to determine the presence of a pathogen causing disease or illness at an early stage in order to treat the animal before the illness or disease has progressed to a stage resulting in irreparable harm or terminal illness. Moreover, these temperature sensing devices have obviated the problem of periodic temperature measurements through anal thermometers and the like.

Temperature sensing devices of the types mentioned above usually include a stem insertable through an opening and into a cavity in the body of the animal. Particularly, it has been recognized that there is cavity in a region behind an animal's ears adjacent to its skull and formed by subcutaneous facia and fat in which the stem may be inserted. At its outer end, the stem is provided with some form of temperature indicating device providing visual warning of temperature change, and which is responsive to a member in the stem for indicating temperature change in the animal body. These devices are designed for relatively permanent implant in the animal.

One of the primary problems with the use of these devices is that the opening never fully heals with the relatively permanent temperature indicating mechanism disposed in the animal's body through the opening. In addition, the opening serves as a pathway for foreign substances, typically the passage of bacteria which may cause an infection in the animal and which can result in illness of the animal. In addition, percutaneous installation of an apparatus formed of a material which is foreign to the living body tissue has resulted in the rejection of the apparatus as a result of migration through the opening of bacteria, germs, foreign particles, moisture and other foreign substances present on the surface of the animal body.

There have been attempts to utilize powder or salves or liquid medications injected into or located around the surface of an incision which receives the percutaneous member in order to promote healing. However, the wetting from the wound and the liquification of the medication on the exterior tissue causes migration of the medication into the wound which also carries undesirable surface contaminants into the animal body. In this respect, the wound serves as a reversely acting "wet wick" which not only would carry in the medication, but also the various undesirable surface contaminants and which subsequently may produce infections or other conditions detrimental to the health of the animal. In this respect, the wet wound acts somewhat in the manner of a wick to foreign substances since it has a tendency to pull foreign substances. Further, since the wet wound tends to pull such substances inwardly, it acts as a reversely acting wet wick.

Temperature sensing devices and other devices for relatively permanent implant in an animal may include expandable arms which are expandable upon a manual screwing action on a portion of the stem external to the animal. However, it is difficult to determine when the arms have fully expanded so that overscrewing and necrosis does not result.

The present invention overcomes these and other problems in providing a foreign substance barrier device which effectively restrains the migration of foreign substances of any origin into the animal's body through an incision formed therein and which thereby reduces the rejection of a percutaneous member inserted through the incision and into the animal's body. The device of the present invention also serves as an effective indicator or tightness so that overscrewing or other tightening action does not occur which would otherwise result in necrosis.

OBJECTS OF THE INVENTION

It is, therefore, the primary object of the present invention to provide a barrier device which surrounds an opening in living animal tissue inhibiting foreign substance migration through an opening, and which also promotes healing thereof.

It is another object of the present invention to provide a barrier device of the type stated which is formed of a resilient, somewhat deformable material, so as to conform to the surface of the animal's body surrounding the opening and to a portion of a percutaneous member for relatively permanent implant in the animal's body.

It is a further object of the present invention to provide a barrier device of the type stated which is relatively permanently installed with percutaneous members of the type providing temperature change indication in the animal's body.

It is an additional object of the present invention to provide a barrier device of the type stated which fully conforms to the exterior surface of the animal tissue and fully covers an opening in the animal tissue to thereby prevent pathogenic conditions.

It is yet another object of the present invention to provide a barrier device of the type stated which enables visual indication of the degree of tightness with which a member for relatively permanent implant is fastened within an animal body, thereby aiding in avoiding conditions of necrosis.

It is also an object of the present invention to provide a method of inhibiting foreign substance migration through an opening in living animal tissue, and to promote healing thereof by utilizing a flexible, somewhat deformable barrier element around said opening.

It is another salient object of the present invention to provide a method of visually indicating the degree of tightness with which a member for relatively permanent implant is secured within the living tissue of an animal by use of a relatively compressible and flexible device.

With the above and other objects in view, our invention resides in the novel features of form, construction, arrangement and combination of components as described and pointed out in the claims.

SUMMARY OF THE DISCLOSURE

The present invention provides a relatively permanent barrier device which is designed for use with a relatively rigid member, such as a retaining member, designed for relatively permanent implant in living animal tissue of a living animal. The barrier device is provided with a size and shape to surround an opening in living animal tissue and serve as a barrier to foreign substance migration through the opening. In addition, the barrier device has been found to also aid in promoting the healing of an incision or other opening in the living animal tissue.

The barrier device is formed of a somewhat flexible and resilient material, and is preferably deformable to at least substantially and preferably fully conform to the exterior surface of the animal and to at least generally conform to a surface of the member for relatively permanent implant. In the preferred aspect, the material used in the barrier device is a sponge-like material. However, it should be understood that other forms of material could be utilized, as for example, plural layers of cloth, e.g., cotton materials or the like. In this respect, all materials which are flexible and deformable including sponge materials and which permit some air flow therethrough will be referred to as "cloth-like".

The barrier device is preferably provided with an aperture in order to receive the member for relatively permanent implant which is typically a rigid or relatively rigid member, as for example, a retaining member. In the preferred embodiment of the invention, the member for relatively permanent implant is a percutaneous member which may be in the form of a temperature sensing and indicating device.

In a typical construction where the percutaneous member is a temperature indicator, the member includes an elongate stem which is insertable through the aperture in the barrier element, and through the opening and into a cavity in the animal's body. The stem would include some means of sensing temperature, and particularly sensing temperature changes in the animal's body. Again, the opening into which the stem is inserted should communicate with a body cavity which is reasonably representative of the temperature and hence temperature changes in the animal's body. At the outer end, the stem carries an enlarged head or other portion which provides visual temperature change indication, as for example, by presenting visual color changes.

It should be understood that the term "retaining member" is used in a broad and generic sense to include any form of device inserted through an incision or other opening in living tissue, including, for example, fasteners for identification tags, reflectors, or the like. In addition, the term "retaining member" will be deemed to include any other member for relatively permanent implant which extends into or through an opening in living tissue since the member will at least extend through the percutaneous layer. Thus, for example, the barrier device of the present invention could be used with a member designed to extend through openings formed in the lips of the vulva, openings formed in the ear of an animal, or the like.

The barrier device is highly effective in inhibiting foreign substance from migrating through the incision or other opening into the animal body, but which permits the flow of relatively clean air through the opening by adequately filtering and trapping atmospheric contaminants. By substantially preventing migration into the animal body of foreign substances which may contain disease causing pathogens, normal body rejection of the percutaneos member is effectively reduced. In this way, the barrier device also serves to provide more rapid healing.

The barrier device of the present invention functions quite effectively in preventing foreign substance migration through an opening in living animal tissue by virtue of at least its resiliency and compressibility. In this way, the barrier device can substantially conform to the surface of the animal and preferably fully conform to the surface of the animal at least surrounding the opening, so that it effectively filters any foreign substance. It has been found in connection with the present invention that even a passage of no more than two microns in cross-sectional dimension formed between the barrier device and the exterior surface of the animal tissue leading to the opening or incision is sufficient for pathogenic substances to migrate to and through the opening. Inasmuch as the barrier device is always in contact with the external tissue of the animal surrounding the opening, there is no possibility for this foreign substance migration to occur. The barrier device should remain sufficiently close to the animal tissue in a periphery surrounding the opening in the animal body so that there is no space leading to the opening which is generally larger than about one micron.

The barrier element can be produced in a wide variety of sizes and configurations to lend to a desired application. In addition, the device is quite easy and simple to apply in essentially any position on the animal's body. Even more so, by properly selecting a barrier material, e.g. a sponge-like material, the barrier element retains its effectiveness notwithstanding any environmental conditions, as for example, rain, excessive high and low temperatures, salt water, and the like.

When the barrier device is installed with the member for relatively permanent implant, it should be compressed to a thickness at least sufficient to always remain in contact with the exterior surface of the animal tissue in all portions of the tissue surrounding the opening. The amount of compression required will be dependent upon several conditions, as for example, the nature of the material forming the barrier device and the resiliency thereof and the activity of the animal. For example, in an animal where substantial activity is likely with a resultant movement or displacement of the exterior surface of the animal tissue, the barrier device should be compressed to a greater degree. In general, the barrier device should be compressed to at least fifty percent of its original thickness. However, if the animal in which the barrier device is used is relatively immobile, then the amount of compression of the barrier device could be as little as about ten percent.

The amount of compressibility of the barrier device during implant is also a function of the age of the animal or similar condition. Thus, in relatively young animals, the member for relatively permanent implant would be tightened only to the extent that there is room for additional compressibility of the barrier device as the animal grows. However, the barrier device should always at least substantially conform to the surface of the animal in all portions surrounding the opening in the animal tissue.

The term "substantially conform" in this sense is used to mean that the barrier device will engage the exterior surface of the animal tissue in all portions surrounding the opening to an extent sufficient to prevent foreign substance migration between the barrier element and the exterior surface of the animal tissue to and through the opening in the animal tissue.

The barrier element should be formed of a bio-compatible material which will not interfere with body functions or otherwise cause discomfort to the animal. In addition, this material should be formed with a cell structure such that it does not function as a wick which would cause migration of foreign substances into the body cavity. Thus, foam rubber may be used effectively as a barrier element. A highly effective material for use as a barrier element is an ostomy sponge used in surgical procedures on human beings. In like manner, carbon containing sponges are highly effective.

If desired, the barrier element may be impregnated with any ingredient to increase its resistance to environmental deterioration, as for example, nylon fibers, carbon or the like. In addition, the barrier may be impregnated with any substance to increase the desired bio-compatability of the barrier element.

As indicated previously, the barrier device of the present invention is generally always used with a member for relatively permanent implant, as for example, a percutaneous member. Further, these members include an elongate stem having an enlarged head which engages the exterior surface of the animal body, along with some mechanism for engaging the interior surface in the opening of the animal body and thereby effect the clamping of the retaining member to the animal for relatively permanent implant. Generally, these retaining members include means for manually tightening the retaining member and may include means for adjusting the amount of tightness with which the retaining member is implanted in the animal body.

The barrier device of the present invention also effectively serves as a compressibility indicator and, in other words, an indicator of the amount of tightness with which the retaining member is held within the animal body. In this way, the party installing the retaining device in the animal body can carefully observe the amount of compression of the barrier device and thereby implant the retaining member with the desired amount of tightness. Moreover, by visually observing the amount of compression as determined by the barrier device, it is possible to avoid over-tightening and the resultant necrosis which oftentimes results in substantial injury to the animal.

The barrier device is highly effective in being used in combination with various retaining members, e.g. the percutaneous members described above, as well as fasteners, toggles or the equivalent. Moreover, the barrier device can be used in combination with a hair deflection collar, identification tag, sensor mechanism, or other unit at the site of an incision or opening in living animal tissue, and which is not an irritant to the animal.

This invention possesses many other advantages and has other purposes which may be made more clearly apparent from a consideration of forms in which it may be embodied. These forms are shown in the drawings accompanying and forming part of the present specification. They will now be described in detail, for the purpose of illustrating the general principles of the invention; but it is to be understood that such detailed descriptions are not to be taken in a limiting sense.

BRIEF DESCRIPTION OF THE DRAWINGS

Having thus described the invention in general terms, reference will now be made to the accompanying drawing in which:

FIG. 1 is a schematic vertical sectional view, showing the implant of a percutaneous member and the barrier device of the present invention used around an opening in living animal tissue;

FIG. 2 is a side elevational view of the percutaneous member with a barrier device in the unlocked and insertable position;

FIG. 3 is a vertical sectional view, somewhat similar to FIG. 2, and showing the percutaneous member in a locked position into the animal's body;

FIG. 4 is a perspective view of one form of barrier device used in the present invention; and FIG. 5 is a side elevational view showing the use of a pair of barrier devices of the present invention;

FIG. 6 is a somewhat schematic view of a tag attached to the ear of an animal by a pair of fasteners similar to that illustrated in FIG. 5; and FIG. 7 is a vertical sectional view taken along line 6—6 of FIG. 5.

BRIEF DESCRIPTION OF A PREFERRED EMBODIMENT

Referring now in detail and by reference characters to the drawings which illustrate a preferred embodiment of the present invention, A designates a barrier device used in conjunction with a percutaneous member P. The barrier device A is formed of a sponge-like material, and in the embodiment as shown, is formed as a cylindrically shaped disc 10. The disc 10 is provided with a central aperture 12, extending therethrough for reasons which will presently more fully appear.

The percutaneous member P generally comprises a retaining assembly 14, including an elongate cylindrically shaped sleeve 16, which is integrally formed at its upper end with an outwardly struck anularly extending retaining flange 18. At its lower end, the elongate sleeve 16 is provided with a plurality of bendable securement strips 20 which are integral with the sleeve 16 and extend downwardly therefrom. In this embodiment of the invention, four such bendable strips 20 are shown, although it should be understood that any number of the strips could be employed.

The bendable securement strips 20, although integral with the sleeve 16, are sufficiently thin but nevertheless sufficiently durable so that they form a hinged connection 22 at the lower end of the sleeve 16. In addition, intermediate their ends, the bendable securement strips 20 are provided with a reduced section 24, constituting a mid-hinge section. At their lower ends, the bendable securement strips 20 integrally merge into a cylindrically shaped nut 26.

Provided for insertion into the retaining assembly 14, is a locking bolt 30 which includes an elongate shank 32, and having a lower threaded portion 34 which extends through the nut 26. In this respect, the nut 26 is provided with an interior threaded portion which matches the externally threaded section 34 on the bolt 30. At its upper end, the shank 32 integrally merges into an enlarged head 36, which has a lower face bearing against the upper surface of the retaining flange 18 in the manner as illustrated in FIGS. 1–3 of the drawings.

A suitable temperature sensing means (not shown) may be internally included within the locking bolt 30. This temperature sensing means could adopt the form of a temperature responsive thermometer, or like construction. In addition, the temperature sensing means does not necessarily have to measure temperature directly, and it could measure other body functions. For example, the temperature sensing means could measure pH changes in terms of a relationship between body pH and body temperature, and thereby provide an indication of temperature change. One such form of temperature sensing means could be that employed is more fully described in copending application Ser. No. 672,669 filed Apr. 1, 1976 (now U.S. Pat. No. 4,083,364).

The enlarged head 36 is provided with a central recessed portion or so-called "dished-out" portion 38 which may receive a temperature indicating means 40. In this case, the temperature indicating means may also adopt the form of temperature change indicator set forth in the above identified copending application. In addition, the temperature indicating means could adopt the form of a material which is colorless and becomes colored upon the temperature being changed or otherwise a material which changes from one color to another in response to a temperature change. A cap 42 may be disposed over the enlarged head 36, and snap-fitted, or otherwise secured, within the recess 38. In this respect, the cap 42 should be transparent so as to enable the viewer to observe any indication of temperature change.

In this respect, the term temperature measuring actually is used in a broad sense to indicate temperature detecting, and in the preferred embodiment, detection of temperature changes. However, if desired, it should be understood that a more elaborate temperature indicating mechanism which actually provides direct read-out of temperature could be provided. However, it is generally only necessary for the keeper of the animals to be able to visually observe a temperature change by mere casual observation of the temperature indicating means, and for this purpose a prominent and readily apparent temperature change indicator is desirable.

In order to insert percutaneous member P into an animal body, an incision or similar opening is formed by piercing through a layer of tissue 50, formed of gristle and hide, by means of a suitable surgical instrument. An opening 52 thus formed would be appropriately located to lead into and communicate with a suitable cavity 54, located beneath the tissue 50.

A preferred region to form the incision is near the junction of the back portion of the ear and the skull in an animal's head which leads into a cavity. This cavity is protected by tissue including gristle and hide, and is also isolated on the side portions by tissue and bone. Moreover, by virtue of the isolation of the cavity, it is very closely related to the animal body temperature, with the difference in temperature being in the order of only one degree F. This particular region may be accurately described as the area bounded cranially by the posterior border of the conchal cartilage and caudally by the anterior border of the cleido-occipitalis muscle. The area is composed of skin, sub-cutaneous fascia and fat. However, as indicated previously, the percutaneous device could be inserted essentially anywhere through the animal tissue into a body cavity.

The percutaneous member P may also utilize a relatively flat retaining plate 56, and in which the bendable strips 20 and the sleeve 16 are inserted through a central aperture formed within the plate 56. In order to physically attach the percutaneous member to the animal's body, the bendable strips 20 and the sleeve 16 are passed through the central aperture 12 in the barrier element A, in order to form the assembly as more fully illustrated in FIG. 2 of the drawings. Thereafter, the assembly is inserted through the aperture in the plate 56, through the opening 52 and into the body cavity 54.

After the assembly is inserted as described, the locking bolt 30 may be turned so that the locking nut 26 and the bendable strips are threadedly moved upwardly along the threaded section 34 of the shank 32. As this occurs, the bendable strips 20 will be biased outwardly to assume the position as illustrated in FIG. 3 of the drawings. Moreover, the bendable strips 20 will thereby form the upper leg portions 58 which engage the upper surface of the cavity 54, in the manner as illustrated in FIG. 1 of the drawings.

In accordance with this construction, it can be observed that the percutaneous member can be relatively permanently implanted in the animal's body. Moreover, and as indicated above, it is not necessary for the percutaneous member to serve as a temperature indicator, and it could in fact serve as any form of fastener or other member such as a hairguard or as a means for securing an identification tag, or the like. In this respect, the term "relatively permanent" is used in a sense to imply that the percutaneous member, and for that matter, the barrier element, are not merely applied for a temporary condition. Specifically, with respect to the barrier device, this device is not applied in a temporary condition in the same manner that a bandage or a similar protective gauze or the like would be applied for ultimate removal upon cure of the wound. Thus, the barrier device will remain in its fastened position so long as the percutaneous member is used. It is possible to remove the percutaneous member as previously described, by merely turning the locking bolt 30 in the opposite direction to cause the nut 26 to shift downwardly along the threaded section 34. After removal of the retaining assembly 14, it is possible to install a new barrier device, if desired.

It can be observed, when the percutaneous member is relatively permanently fastened into position in the animal body, the barrier element 10 will deform in order to conform to the surface of the animal body and will also conform to the engaging portion of the percutaneous member as for example, the plate 56. The plate 56 may not necessarily form part of the percutaneous member, but could adopt the form of an animal tag. Moreover, the barrier element can be sufficiently large so that it extends beyond the incision or opening and protects against any passage of foreign substance into the cavity 54. However, the barrier element 10 is sufficiently porous so as to permit air to pass therethrough and into the cavity 54 in order to promote healing. As indicated previously, any foreign substance in the air will be effectively filtered out by the barrier element 10.

Considering the percutaneous member P of the present invention, it can be observed that the bendable securement strip 20 forms wings which engage the interior surface of the animal tissue, in the manner as illustrated in FIG. 1 of the drawings. However, it can also be observed that by over-tightening the shank 32, it is possible to engage the wings too tightly against the interior surface of the tissue, thereby providing too great a tightness or clamping action.

The barrier device of the invention also effectively serves as a compression indicator. As indicated above, many of the members for relatively permanent implant in animal bodies utilize securement strips 20 or a similar mechanism which expands to engage an interior surface of the animal, and thereby hold the member in place. However, unless considerable care is used during the implant of the percutaneous member or similar member for relatively permanent implant, the expandable section could be tightened excessively. This would result in an undesirable condition of necrosis, e.g. tissue death resulting from insufficient fluid circulation. By observing the amount of compression of the barrier device during the tightening action, it is possible to avoid over-tightening and the resultant necrosis. The device normally should be tightened during implantation to a range where the barrier device also allows the percutaneous member to be adjustable during implantation to account for various hide thicknesses.

The amount of compression desired in the barrier device will, of course, vary, depending upon the materials used in the formation of the barrier device. A relatively compressible and resilient material would not be tightened, i.e., compressed, as much as a material which is not so resilient or compressible. When the foam is used as the barrier device, it is oftentimes desirable to tighten the percutaneous member so that the barrier device has a resultant thickness of about 15 mils to about 60–100 mils in order to obtain the proper type of sealing action against the exterior surface of the animal tissue. In many cases, it may be desirable to tighten the percutaneous member until the barrier element compresses to a point where the enlarged head 36 begins to tilt slightly upwardly around the periphery.

As indicated previously, when installing the percutaneous member, or other member for relatively permanent implant in an animal, it may be desirable to account for the age of the animal so that as the animal grows, the device will become more tightly affixed to the animal.

As also indicated previously, it is most important to have the barrier element substantially conform to the surface of the tissue of the animal so that there is essentially no passage or opening between the barrier element and the exterior surface of the animal. In this way, while air is permitted to flow through the barrier element, it nevertheless functions as an effective filter for external contaminants, which might otherwise cause pathogenic conditions or other disorder.

Some of the materials used in the formation of the barrier element were described above. One particularly effective material used in the formation of the barrier device is an ester-type polyurethane. Generally, the material used should have a porosity of about 50 to about 110 pores per linear inch (PPI), and preferably a porosity of about 50 to about 100 PPI. However, the most effective porosity is that near about 100 PPI. Sponge-like materials should be formed in a thermal reticulation, or so-called "zapped" process, as opposed to a chemical quench reticulation process.

It is also possible to impregnate the barrier element with a bactericidal agent in order to further inhibit bacterial migration. However, any such agent should not increase or cause any wetting action since this would only serve to enhance foreign substance migration. In many cases, it may be desirable to spray the area of the hide receiving the implant with a dry bactericidal agent.

In many cases, it may be desirable to spray the surface of the animal with a material to adhere foreign substances on the surface of the animal and to keep the hair and hide away from the portion of the tissue while making an incision. Typical hairspray is not acceptable because it is generally not bio-acceptable. However, there are commercially available sprays which are effective for this purpose. Further, it is possible to apply a drug to the surface of the animal tissue in proximity to the area of the wound in order to aid in drying of wound secretions. In like manner, this drug could also be incorporated into the material forming the barrier device.

The percutaneous member may also be designed to permit the introduction of medicinal or other substances, such as hormones or the like, into the animal body without any interference by the barrier element 10.

FIG. 5 of the drawings illustrates an embodiment of the invention where a pair of barrier devices of the present invention are used with a member 70 for relatively permanent implant through an opening formed in or incised in an animal. In this case, the member may not extend only to a percutaneous layer, but will nevertheless be deemed to be a percutaneous member as defined herein.

The member 70 is shown as extending through an opening 72 incised into ear tissue 74 of an animal. In this case, the member 70 is provided with both shank 75 having a pair of threadedly removable caps 76 and 78. Moreover, by reference to FIG. 5, it can be observed that barrier devices are located between the removable caps 76 and 78 and the external hide of the animal ear. While this form of member 70 for relatively permanent implant does not have an expandable section as such, it is still nevertheless important to avoid over-tightening of the caps 76 and 78 on the shank 75. Again, the barrier devices of the present invention will effectively serve as compression indicators for this purpose.

FIG. 6 illustrates a somewhat flexible element 79, which may be in the nature of an animal tag, overlying the ear 74 of an animal and which is secured by two fasteners which both employ barrier elements of the present invention on opposite sides thereof. It can be observed by reference to FIG. 6 that each of the fasteners, designated as 80 are comprised of an elongate shank 82 having threadedly removable caps 84 and 85. Moreover, interposed between flaps 88 forming part of the tag 79 and the external tissue of the animal ear, are barrier elements A of the present invention. Thus, it can be observed that pairs of barrier elements can be connected to opposite sides of a retaining device and can be used in multiples in the manner as illustrated. In each case, it has been found that the use of barrier elements is highly effective in overcoming problems of infection and like dilatorious conditions.

Although the percutaneous member and the use of the barrier element have been described in connection with cattle, it should be understood that they could be used on essentially any form of animal, including goats, sheep and other domestic or semidomestic animals. In a like manner, the device could also be used on any form of wild animal. Again, the term "animal" is used in a broad sense to include birds, fish, and other creatures having living tissue.

Thus, there has been illustrated and described a unique and novel device and method for reducing infection and promoting healing at openings in living animal tissue which receive a percutaneous implant and which therefore fulfills all of the objects and advantages sought therefor. It should be understood that many changes, modifications, variations, and other uses and applications of the device and method will become apparent to those skilled in the art after considering this specification and the accompanying drawings. Therefore, any and all such changes, modifications, variations, and other uses and applications which do not depart from the nature and spirit of the invention are deemed to be covered by the invention which is limited only by the following claims.

Having thus described our invention, what we desire to claim and secure by Letters Patent is:

1. An animal information means adapted for insertion through an opening cut through the skin and into a cavity formed in the subcutaneous fascia of a live animal comprising:

(a) a temperature actuated warning assembly including a fever temperature sensing means, and a fever temperature signaling means;

(b) retaining means for retaining the sensing means in said cavity while exposing the signaling means for view;

(c) a barrier element comprised of a flexible resilient material formed of a bio-compatible material which will not adversely effect body functions to cause discomfort when relatively permanently mounted about the opening in animal tissue, said barrier element being retained by said retaining means against an outer surface of the skin of said animal, said barrier element being relatively deformable to essentially always substantially conform to the exterior surface of said animal and to a portion of the retaining means facing said animal so that said barrier element is generally permanently retained about the opening and generally about at least as long as said member remains in the animal tissue to inhibit migration of foreign substance through said opening and to promote healing thereof, said material forming the element having a cell structure sized so that the element does not function as a wick which would otherwise cause a migration of a foreign substance into said opening, said cell structure also being sized so that it is sufficiently porous to prevent passage of foreign substances into the opening but permits air to pass therethrough and promote healing.

2. The information means of claim 1 further characterized in that means is responsive to the temperature sensing means to expose said signaling means to view indication of a temperature in the animal.

3. The animal information means of claim 1 further characterized in that the retaining means includes an externally disposed flange and a cooperating means within the cavity for securing the flange against the hide of the animal.

4. The animal information means of claim 1 further characterized in that said barrier element is relatively compressible.

5. The animal information means of claim 1 further characterized in that the barrier element is sufficiently resilient and compressible to fully cover and always engage the exterior surface of the animal tissue in periphery surrounding the opening even during shifting movement or displacement of the tissue.

6. The animal information means of claim 5 further characterized in that said assembly is capable of being manually tightened within the animal tissue and said barrier element provides a visual indication of the tightness with which the assembly is held in the animal tissue.

7. The animal information means of claim 6 further characterized in that the barrier element engages the animal tissue completely surrounding the opening so that there is no passage between the barrier element and the exterior surface of the animal tissue leading to the opening in the animal tissue which is greater than 1.0 microns in cross section.

* * * * *